United States Patent [19]

Smith

[11] 4,085,221

[45] Apr. 18, 1978

[54] ETHANOLAMINE DERIVATIVES

[75] Inventor: Leslie Harold Smith, Macclesfield, England

[73] Assignee: Imperial Chemical Industries Limited, London, England

[21] Appl. No.: 745,164

[22] Filed: Nov. 26, 1976

[30] Foreign Application Priority Data

Dec. 5, 1975   United Kingdom ............... 50037/75

[51] Int. Cl.$^2$ ..................... A61K 31/38; C07D 307/81
[52] U.S. Cl. .............................. 424/275; 260/306.8 R;
260/326.14 R; 260/330.5; 260/332.2 A;
260/340.3; 260/346.73; 260/347.3; 424/282;
424/285; 548/305
[58] Field of Search .................... 260/346.2 R, 330.5, 260/340.3; 424/285, 278, 275

[56] References Cited

U.S. PATENT DOCUMENTS

| | | | |
|---|---|---|---|
| 3,944,611 | 3/1976 | Smith | 260/562 R |
| 3,957,870 | 5/1976 | Main | 260/562 N |

*Primary Examiner*—Henry R. Jiles
*Assistant Examiner*—Bernard Dentz
*Attorney, Agent, or Firm*—Cushman, Darby & Cushman

[57] ABSTRACT

Novel 1-aryl-2-amidoalkylaminoethanol derivatives which contain at least one heterocyclic substituent, processes for their manufacture, pharmaceutical compositions containing them and a method of using them in the treatment of heart diseases. The compounds possess $\beta$-adrenergic blocking activity. Representative of the compounds disclosed is 2-$\beta$-(2-methylthiazol-4-ylacetamido)ethylamino-1-$\beta$-naphthylethanol.

11 Claims, No Drawings

ETHANOLAMINE DERIVATIVES

This invention relates to new ethanolamine derivatives which possess β-adrenergic blocking activity.

According to the invention there is provided a new ethanolamine derivative of the formula:

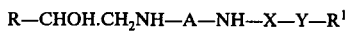

R—CHOH.CH$_2$NH—A—NH—X—Y—R$^1$ wherein A stands for an alkylene radical of from 2 to 12 carbon atoms; wherein X stands for the carbonyl (—CO—) or sulphonyl (—SO$_2$—) radical; wherein Y stands for a direct link, or for an alkylene or alkyleneoxy radical each of up to 6 carbon atoms, or for the imino (—NH—) radical, or for an alkylimino, iminoalkylene, iminoalkyleneoxy or iminoalkylenecarbonyloxy radical each of up to 6 carbon atoms, or (except when R$^1$ stands for the hydrogen atom) for the oxygen atom; and wherein R stands for a heterocyclic radical or for an aryl radical of the formula:

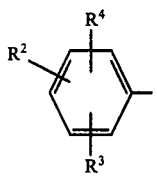

and R$^1$ stands for the hydrogen atom or for an alkyl, alkenyl, halogenoalkyl or cycloalkyl radical each of up to 6 carbon atoms, or for a heterocyclic radical, or for an aryl radical of the formula:

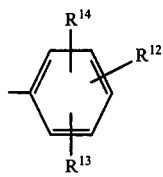

wherein R$^2$, R$^3$, R$^{12}$ and R$^{13}$, which may be the same or different, each stands for a hydrogen or halogen atom, a hydroxy, amino, nitro or cyano radical, an alkyl, hydroxyalkyl, cycloalkyl, alkenyl, alkynyl, alkoxy, alkylthio, cycloalkoxy, alkenyloxy, alkynyloxy or alkanoyl radical each of up to 6 carbon atoms, or an aryl, aryloxy or dialkylamino radical each of up to 12 carbon atoms; or wherein R$^2$ and R$^3$ together, and/or R$^{12}$ and R$^{13}$ together, form the trimethylene, tetramethylene, 1-oxotetramethylene, propenylene, but-2-enylene or buta-1,3-dienylene radical such that together with the adjacent ring they form respectively the indanyl, 5,6,7,8-tetrahydronaphthyl, 5-oxo-5,6,7,8-tetrahydronaphthyl, indenyl, 5,8-dihydronaphthyl or naphthyl radical; wherein R$^4$ and R$^{14}$, which may be the same or different, each stands for the hydrogen atom or for an amidic radical of the formula:

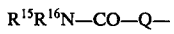
R$^{15}$R$^{16}$N—CO—Q—

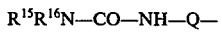
R$^{15}$R$^{16}$N—CO—NH—Q—

R$^{15}$R$^{16}$N—CO—Q$^1$—O— or

R$^{16}$—X—NR$^{15}$—Q— wherein Q stands for a direct link or for an alkylene or alkenylene radical each of up to 6 carbon atoms; wherein Q$^1$ stands for an alkylene radical of up to 6 carbon atoms; wherein R$^{15}$ stands for the hydrogen atom or for an alkyl radical of up to 6 carbon atoms; wherein R$^{16}$ stands for the hydrogen atom, or for an alkenyl, cycloalkyl, hydroxyalkyl or alkoxyalkyl radical each of up to 6 carbon atoms, or for an alkyl, aryl, aralkyl or aralkenyl radical each of up to 10 carbon atoms; provided that at least one of R and R$^1$ stands for a heterocyclic radical; or an acid-addition salt thereof.

It will be observed that the ethanolamine derivative of the invention possesses an asymmetric carbon atom, namely the carbon atom of the —CHOH— group in the ethanolamine sidechain, and it can therefore exist in racemic and optically-active forms. It is to be understood that this invention encompasses the racemic form of the ethanolamine derivative and any optically-active form which possesses β-adrenergic blocking activity, it being a matter of common general knowledge how a racemic compound may be resolved into its optically-active forms and how the β-adrenergic blocking activity of these forms may be determined. It is to be understood that β-adrenergic blocking activity usually predominates in that optically-active form which has the "R" absolute configuration of the said —CHOH— group.

A suitable value for the alkylene radical A is, for example, the ethylene, trimethylene, tetramethylene, hexamethylene, 1-methylethylene, 2-methylethylene or 1,1-dimethylethylene radical. A is preferably the ethylene, 1-methylethylene or 1,1-dimethylethylene radical.

A suitable value for Y when it stands for an alkylene or alkyleneoxy radical is, for example, the methylene, ethylene, methyleneoxy, ethyleneoxy, trimethyleneoxy, 1-methylethylideneoxy or 1-methylpropylideneoxy radical.

A suitable value for Y when it stands for an alkylimino, iminoalkylene, iminoalkyleneoxy or iminoalkylenecarbonyloxy radical is, for example, the methylimino, iminomethylene, iminomethyleneoxy or iminomethylenecarbonyloxy radical.

Y is preferably a direct link or the methylene, methyleneoxy or imino radical.

A suitable value for R or R$^1$ when it stands for a heterocyclic radical is, for example, a mono-, bi- or tricyclic heterocyclic radical in which at least one ring is a 5- or 6-membered saturated or unsaturated hetero-ring containing one, two or three heteroatoms selected from nitrogen, oxygen and sulphur atoms; and in which the second and/or third ring, if present, may be a hetero-ring as defined above or may be a benzene ring; and which heterocyclic radical may optionally contain one or more substituents selected from halogen atoms, for example chlorine and bromine atoms, alkyl, alkoxy, acylamino, carbamoyl and alkanoyl radicals each of up to 6 carbon atoms, for example methyl, ethyl, methoxy, ethoxy, acetamido, methylcarbamoyl and acetyl radicals, aryl and aryloxy radicals each of up to 10 carbon atoms, for example phenyl, p-chlorophenyl and phenoxy radicals, and amino and substituted amino radicals, for example amino, alkylamino, dialkylamino and heterocyclic amino radicals each of up to 6 carbon atoms, for example amino, methylamino, dimethylamino and morpholino radicals; and, where the heterocyclic radical bears an appropriate degree of saturation, which heterocyclic radical may optionally bear one or two oxo substituents.

A particular heterocyclic radical is, for example, a pyrrolyl, furyl, thienyl, imidazolyl, pyrazolyl, oxazolyl, isoxazolyl, thiazolyl, thiadiazolyl, pyridyl, pyranyl, pyrazinyl, pyridazinyl, pyrimidinyl, indolyl, isoindolyl, benzofuranyl, benzothienyl, benzodioxolyl, benzimidazolyl, benzothiazolyl, benzothiadiazolyl, quinolyl, chromanyl, chromenyl, thiochromanyl, benzodioxanyl, carbazolyl or phenothiazinyl radical, for example the 2-pyrrolyl, 2-furyl, 5-p-chlorophenyl-2-furyl, 2-thienyl, 3-thienyl, 2-imidazolyl, 5-methyl-3-pyrazolyl, 2-phenyl-5-methyl-3-pyrazolyl, 2-oxazolyl, 3-isoxazolyl, 2-thiazolyl, 2-p-chlorophenyl-4-thiazolyl, 2-methyl-4-thiazolyl, 4-morpholino-1,2,5-thiadiazol-3-yl, 4-pyridyl, 2-methyl-4-oxo-4H-pyran-3-yl, 3-methyl-2-pyrazinyl, 3-phenyl-2-pyrazinyl, 3-pyridazinyl, 2-p-chlorophenyl-6-methoxypyrimidin-4-yl, 2-indolyl, 3-indolyl, 4-indolyl, 2-methylindol-4-yl, 2,3-dihydro-2-oxo-4-indolyl, 3-oxo-2-phenyl-isiondolin-1-yl, 2-benzo[b]furanyl, 4-benzo[b]furanyl, 2,3dimethyl-4-benzo[b]furanyl, 2-acetyl-7-benzo[b]furanyl, 3-benzo[b]thienyl, 4-benzo[b]thienyl, 5-benzo-dioxolyl, 2-benzimidazolyl, 5-benzothiazolyl, 5-(benzo[c]-[1,2,5]-thiadiazolyl), 2-quinolyl, 1,2-dihydro-2-oxo-5-quinolinyl, 1,4-dihydro-6-methoxy-4-oxo-2-quinolinyl, 1,2,3,4-tetrahydro-2-oxo-5-quinolinyl, 4-oxochroman-8-yl, 4-methyl-2-oxo-2H-chromen-8-yl, thiochroman-8-yl, 1,4-benzodioxan-2-yl, 1,4-benzodioxan-5-yl, 1,4-benzodioxan-6-yl, 1-carbazolyl or 1-phenothiazinyl radical.

A suitable value for $R^1$ when it stands for an alkyl, alkenyl, halogenoalkyl or cycloalkyl radical is, for example, the methyl, ethyl, n-propyl, isopropyl, n-butyl, isobutyl, t-butyl, n-pentyl, n-octyl, allyl, trifluoromethyl, cyclopropyl, cyclopentyl or cyclohexyl radical.

A suitable value for $R^2$, $R^3$, $R^{12}$ or $R^{13}$ when it stands for a halogen atom is, for example, the fluorine, chlorine, bromine or iodine atom.

A suitable value for $R^2$, $R^3$, $R^{12}$ or $R^{13}$ when it stands for an alkyl, hydroxyalkyl, cycloalkyl, alkenyl, alkynyl, alkoxy, alkylthio, cycloalkoxy, alkenyloxy, alkynyloxy or alkanoyl radical is, for example, the methyl, ethyl, n-propyl, hydroxymethyl, 1-hydroxyethyl, cyclopropyl, cyclopentyl, allyl, ethynyl, methoxy, isopropoxy, methylthio, cyclopentyloxy, allyloxy, propargyloxy, formyl or acetyl radical.

A suitable value for $R^2$, $R^3$, $R^{12}$ or $R^{13}$ when it stands for an aryl, aryloxy, or dialkylamino radical is, for example, the phenyl, phenoxy or dimethylamino radical.

A suitable value for Q or $Q^1$ when it stands for an alkylene radical is, for example, the methylene, ethylene, trimethylene, ethylidene or 1-methylethylene radical. A suitable value for Q when it stands for an alkenylene radical is, for example, the vinylene radical.

A suitable value for $R^{15}$ when it stands for an alkyl radical is, for example, the methyl radical.

A suitable value for $R^{16}$ is, for example, the hydrogen atom or the allyl, cyclopropyl, cyclopentyl, cyclohexyl, 2-hydroxyethyl, 3-hydroxypropyl, 2-hydroxy-1-methylethyl, 2-hydroxy-1,1-dimethylethyl, β-methoxyethyl, methyl, ethyl, n-propyl, isopropyl, n-butyl- t-butyl, n-pentyl, n-hexyl, n-nonyl, phenyl, p-tolyl, p-chlorophenyl, benzyl or styryl radical.

A particular value for $R^4$ or $R^{14}$ when it stands for an amidic radical is, for example, the acetamido, propionamido, methanesulphonamido, carbamoyl, carbamoylmethyl, acetamidomethyl, 3-methylureido, 3-n-butylureido, carbamoylmethoxy, N-methylcarbamoylmethoxy or N-β-hydroxyethylcarbamoylmethoxy radical. The amidic substituent $R^{14}$ when present is preferably in the para- position of the benzene ring.

A suitable acid-addition salt of an ethanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin.

One preferred ethanolamine derivative of the invention is a compound of the formula given above wherein A stands for the ethylene, 1-methylethylene or 1,1-dimethylethylene radical, wherein R stands for a phenyl, tolyl or naphthyl radical, wherein $R^1$ stands for a heterocyclic radical, wherein X stands for the carbonyl radical and wherein Y stands for the methylene radical, or an acid-addition salt thereof. $R^1$ is preferably the 2-thienyl, 2-methyl-4-thiazolyl, 2-p-chlorophenyl-4-thiazolyl or 5-p-chlorophenyl-2-furyl radical.

A second preferred ethanolamine derivative of the invention is a compound of the formula given above wherein A stands for the ethylene, 1-methylethylene or 1,1-dimethylethylene radical, wherein R stands for a 5- or 6-membered heterocyclic radical, containing one or two heteroatoms selected from oxygen and sulphur atoms, to which is fused a benzene ring, wherein $R^1$ stands for the unsubstituted phenyl radical or for an alkyl radical of up to 6 carbon atoms, wherein X stands for the carbonyl radical and wherein Y stands for a direct link or for the methylene radical, or an acid-addition salt thereof. The heterocyclic radical R is preferably the 2-benzo[b]furyl, 3-benzo[b]thienyl or 1,4-benzodioxan-2-yl radical and the group —Y—$R^1$ is preferably the ethyl, isopropyl or benzyl radical.

Specific ethanolamine derivatives of the invention are those hereinafter described in the Examples. Of these, preferred compounds by virtue of their high cardioselective β-adrenergic blocking activity (as hereinafter defined) are 2-β-(2-p-chlorophenylthiazol-4-ylacetamido)ethylamino-1-phenylethanol, 1-(benzo[b]-fur-2-yl)-2-(β-isobutyramidoethyl)-aminoethanol, 2-β-(2-methylthiazol-4-ylacetamido)ethylamino-1-p-tolylethanol, 2-β-(2-methylthiazol-4-ylacetamido)ethylamino-1-β-naphthylethanol, 1-(benzo[b]fur-2-yl)-2-(β-propionamidoethyl)aminoethanol, 1-(1,4-benzodioxan-2-yl)-2-(β-isobutyramidoethyl)aminoethanol and 1-(benzo[b]fur-2-yl)-2-(1-methyl-2-phenylacetomidoethyl)aminoethanol, and the acid-addition salts thereof.

The ethanolamine derivative of the invention may be manufactured by any chemical process publically-known to be useful for the manufacture of chemically-analogous compounds.

According to a further feature of the invention there is provided a process for the manufacture of the ethanolamine derivative of the invention which comprises assembling in sequence, by chemical methods known to be useful for this purpose, the four radicals:

i. a 1-hydroxyethyl radical of the formula:

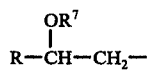

wherein R has the meaning stated above and wherein R⁷ stands for hydrogen or for a protecting group;

ii. an imino radical of the formula —NH⁸—, wherein R⁸ stands for hydrogen or for a protecting group;

iii. a radical of the formula —A—NR⁹— wherein A has the meaning stated above and wherein R⁹ stands for hydrogen or for a protecting group; and iv. a radical of the formula —X—Y—R¹ wherein R¹, X and Y have the meanings stated above;

whereafter if one or more of R⁷, R⁸ and R⁹ stands for a protecting group, the one or more protecting groups are removed.

The various stages of the assembly may be carried out in any possible order. Thus, for example:

a. A compound of the formula:

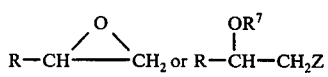

wherein R and R⁷ have the meanings stated above and wherein Z stands for a displaceable radical, or a mixture of such compounds, may be reacted with an amine of the formula:

wherein A, R¹, R⁸, R⁹, X and Y have the meanings stated above, or with a precursor of such an amine.

A suitable value for Z is, for example, a halogen atom, for example the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical.

The reaction may be carried out at ambient temperature or it may be accelerated or completed by the application of heat, for example by heating to a temperature of 90°-110° C.; it may be carried out at atmospheric or at an elevated pressure, for example by heating in a sealed vessel; and it may be carried out in an inert diluent or solvent, for example an alcohol, for example methanol, ethanol, n-propanol or isopropanol, or an excess of the amine may be used as diluent or solvent.

Either compound used as starting material, or a mixture thereof, may be obtained by the reduction, for example by means of sodium borohydride or aluminium isopropoxide, of a compound of the formula

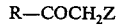

wherein R and Z have the meanings stated above. This compound in turn may be obtained from the corresponding ketone derivative either directly, when Z stands for a halogen atom, or via the corresponding hydroxy compound of the formula R—COCH₂OH wherein R has the meaning stated above.

b. A compound of the formula:

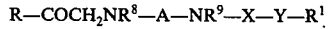

wherein A, R, R¹, R⁸, R⁹, X and Y have the meanings stated above, may be reduced.

The reduction may be carried out by means of a metal borohydride, for example sodium borohydride, in an appropriate diluent or solvent, for example methanol, or by means of catalytic hydrogenation, for example hydrogen in the presence of a palladium, platinum or nickel catalyst.

The starting material may be obtained by the reaction of a compound of the formula

wherein R and Z have the meanings stated above, with an amine of the formula:

wherein A, R¹, R⁸, R⁹, X and Y have the meanings stated above, or with a precursor of such an amine, in an appropriate solvent, for example dioxan or methanol.

c. A compound of the formula:

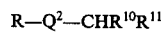

wherein R has the meaning stated above, wherein Q² stands for the carbonyl (—CO—) radical or for a radical of the formula:

wherein R⁷ has the meaning stated above, and wherein either R¹⁰ and R¹¹ together form the oxo (=O) radical, or wherein R¹⁰ and R¹¹, which may be the same or different, each stands for the hydroxy radical or for an alkoxy radical or up to 6 carbon atoms, may be reacted with an amine of the formula:

wherein A, R¹, R⁸, R⁹, X and Y have the meanings stated above, under reducing conditions.

Suitable reducing conditions are provided by, for example, an alkali metal borohydride, for example sodium borohydride, in an appropriate diluent or solvent, for example methanol or ethanol, or by, for example, hydrogen in the presence of a catalyst, for example a platinum, palladium or nickel catalyst.

The starting material wherein Q² stands for the carbonyl radical may be obtained by the oxidation of an acetophenone derivative of the formula

wherein R has the meaning stated above, with selenium dioxide in an appropriate solvent, for example aqueous dioxan, optionally followed by acetal or hemiacetal formation. The starting material wherein Q² stands for a radical of the formula —CHOH— may be obtained by the reduction of the acetal of the corresponding compound wherein Q² stands for the carbonyl radical.

d. The series of reactions described under (a) or (b) or (c) above may be carried out except that an amine of the formula R⁸NH₂ is used in place of an amine of the formula:

it being understood that when R⁸ stands for hydrogen the amine is ammonia. The final product obtained, which has the formula:

$$R-\overset{OR^7}{\underset{|}{CH}}-CH_2NHR^8$$

wherein R, $R^7$ and $R^8$ have the meanings stated above, may alternatively be obtained, when $R^8$ stands for hydrogen, by the reduction of, for example, a compound of the formula:

$$RQ^2CN$$

or $$RQ^2CH_2NO_2$$

wherein R and $Q^2$ have the meanings stated above (which compound may be obtained, when $Q^2$ stands for the —CHOH— radical, by the reaction of a corresponding aldehyde derivative with respectively, hydrogen cyanide or nitromethane), or by the reduction of an oxime of the formula:

$$RQ^2CH=NOH$$

wherein R and $Q^2$ have the meanings stated above (which oxime may be obtained by conventional means from the corresponding aldehyde, or by the reduction of any other suitable compound which contains a group reducible to a primary amino group, for example a diazo or azido group).

The radical —A—$NR^9$—X—Y—$R^1$ may then be inserted as a separate step, for example either by the reaction of the above final product with a compound of the formula:

$$Z-A-NR^9-X-Y-R^1$$

wherein A, $R^1$, $R^9$, X, Y and Z have the meanings stated above, or, by the reaction under reducing conditions of the same final product with a carbonyl compound of the formula:

$$A^1-CO-A^2-NR^9-X-Y-R^1$$

wherein $R^1$, $R^9$, X and Y have the meanings stated above and wherein $A^1$ stands for hydrogen or for an alkyl radical and $A^2$ stands for an alkylene radical such that the radical $$-\overset{A^1}{\underset{|}{CH}}-A^2-$$

has the same meaning as is stated above for A.

The reaction involving a compound of the formula:

$$Z-A-NR^9-X-Y-R^1$$

may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenation catalyst, for example palladium or platinum, it an inert diluent or solvent, for example in one or more solvents selected from water, ethanol and an excess of the carbonyl compound used as starting material; or by the presence of an alkali metal borohydride, for example sodium borohydride or lithium cyanoborohydride, in an inert diluent or solvent, for example in one or more solvents selected from water, ethanol, methanol and an excess of the carbonyl compound used as starting material. It is to be understood that when in the starting material R or $R^1$ stands for a hydrogenolysable heterocyclic radical, or $R^1$ or $R^{16}$ stands for an alkenyl radical, or one or both of $R^2$ and $R^3$ stands for a halogen atom or for a nitro, cyano, alkenyl, alkynyl, alkenyloxy, alkynyloxy, alkylthio or alkanoyl radical, hydrogen and a hydrogenation catalyst are preferably not used to provide the reducing conditions, in order to prevent the radical R, $R^1$, $R^2$, $R^3$ or $R^{16}$ from being affected by catalytic hydrogenation.

e. The series of reactions described under (a), (b), (c) or (d) above may be carried out except that an amine containing a radical of the formula:

$$HNR^8-A-NHR^9$$

wherein A, $R^8$ and $R^9$ have the meanings stated above, is used in place of an amine of the formula:

$$NHR^8-A-NR^9-X-Y-R^1$$

or the reaction described under (d) above may be carried out except that the radical —A—$NHR^9$ is inserted in place of the radical —A—$NR^9$—X—Y—$R^1$. The amidic linkage —$NR^9$—X— may then be formed as a separate step by reaction of the resulting product, which has the formula:

$$R-\overset{OR^7}{\underset{|}{CH}}-CH_2NR^8-A-NHR^9$$

wherein R, $R^7$, $R^8$, $R^9$ and A have the meanings stated above, with a compound of the formula:

$$Z^1-X-Y-R^1$$

wherein $R^1$, X and Y have the meanings stated above and wherein $Z^1$ stands for a displaceable radical, or, when X stands for the carbonyl radical and Y stands for the imino radical, with an isocyanate of the formula OCN—$R^1$, wherein $R^1$ has the meaning stated above.

The displaceable radical $Z^1$ may be a halogen atom, for example the chlorine or bromine atom, or an alkoxy radical, for example the methoxy or ethoxy radical, or it may be the oxygen atom such that the compound $(R^1-Y-X)_2Z^1$ is an acid anhydride.

The reaction to form the amide linkage may be carried out in an inert diluent or solvent, for example toluene or tetrahydrofuran.

The intermediate product of the formula:

$$R-\overset{OR^7}{\underset{|}{CH}}-CH_2NR^8-A-NHR^9$$

may, when $R^9$ stands for hydrogen, alternatively be obtained by, for example, the reduction of the nitro, cyano or carbamoyl radical of a compound of the formula:

$$R-\overset{OR^7}{\underset{|}{CH}}-CH_2NR^8-A^3-Z^2$$

wherein R, $R^7$ and $R^8$ have the meanings stated above, wherein $A^3$ stands for an alkylene radical such that —$A^3CH_2$— has the same meaning as is stated above for A and wherein $Z^2$ stands for the —$CH_2NO_2$, —CN or —$CONH_2$ radical.

f. A compound wherein one or more of $R^7$, $R^8$ and $R^9$ stands for a protecting group may be prepared by the series of reactions described under (a), (b), (c), (d) or (e) above. Alternatively, a suitable protecting group may be introduced by conventional means into an intermediate compound at any stage preceding the final stage.

A suitable value for $R^7$ when it stands for a protecting group is, for example, a hydrogenolysable radical, for example an α-arylalkyl, α-arylalkoxycarbonyl or α-arylalkoxymethyl radical, for example the benzyl, benzyloxycarbonyl or benzyloxymethyl radical, or an acyl radical, for example an alkanoyl radical or up to 20 carbon atoms, for example the acetyl, t-butoxycarbonyl or 2,2,2-trichloroethoxycarbonyl radical, or an aroyl radical of up to 10 carbon atoms, for example the benzoyl radical, or an α-alkoxyalkyl radical (that is, a radical which forms with the adjacent oxygen atom an acetal radical), for example the tetrahydropyranyl radical, or a tertiary alkyl radical, for example the t-butyl radical.

A suitable value for $R^8$ when it stands for a protecting group is, for example, a hydrogenolysable or tertiary alkyl radical as defined for $R^7$, or a relatively easily hydrolysable acyl radical, for example the 2,2,2-trichloroethoxycarbonyl or t-butoxycarbonyl radical. It is to be understood that when $R^8$ stands for an acyl radical, this radical must be removable under conditions which will not destroy the amidic linkage —NH—X—.

Alternatively, $R^7$ and $R^8$ may be joined together so that one protecting group serves to protect both the oxygen and nitrogen atoms. Such protecting group may be, for example, a radical of the formula

—$CHR^6$—,

wherein $R^6$ stands for hydrogen, or for an alkyl radical of up to 4 carbon atoms or an aryl radical of up to 10 carbon atoms, such that it forms, together with the adjacent oxygen and nitrogen atoms and the two adjacent carbon atoms, an oxazolidine nucleus.

A suitable value for $R^9$ when it stands for a protecting group is, for example, a hydrogenolysable or tertiary alkyl group as defined for $R^7$ or $R^8$.

The hydrogenolysable protecting group $R^7$, $R^8$ or $R^9$ may be removed, for example, by catalytic hydrogenation, for example by hydrogenation in the presence of a palladium-on-charcoal catalyst, in an inert diluent or solvent, for example ethanol or aqueous ethanol. The process may be accelerated or completed by the presence of an acidic catalyst, for example hydrochloric or oxalic acid.

The acyl protecting group $R^7$ or $R^8$ may be removed by hydrolysis in the presence of a base, for example an alkali metal hydroxide, in a diluent or solvent, for example water, methanol, ethanol or a mixture thereof. It is to be understood that the hydrolytic conditions used must be sufficiently mild to avoid hydrolysis of the amidic linkage —NH—X—.

The α-alkoxyalkyl protecting group $R^7$ or the protecting group —$R^6CH$— formed by $R^7$ and $R^8$ taken together may be removed by hydrolysis in the presence of an acid, for example a mineral acid, for example aqueous hydrochloric acid, and the hydrolysis may be carried out at a temperature of up to 100° C.

The tertiary alkyl protecting group $R^7$, $R^8$ or $R^9$, or the acyl protecting group $R^7$ or $R^8$ when it stands for a tertiary alkoxycarbonyl radical, of example the t-butoxycarbonyl radical, may be removed by treatment with an acid, for example hydrogen chloride, in anhydrous conditions, for example in ethereal solution.

It is to be understood that a compound wherein the substituent $R^2$, $R^3$, $R^{12}$ or $R^{13}$ is a reactive radical may be converted into a different compound wherein $R^2$, $R^3$, $R^{12}$ or $R^{13}$ is a different substituent. Thus, for example, a compound wherein one or more of $R^2$, $R^3$, $R^{12}$ and $R^{13}$ stands for a nitro, alkenyl, alkynyl, alkenyloxy, alkynyloxy or alkanoyl radical may be reduced to the corresponding compound wherein one or more of $R^2$, $R^3$, $R^{12}$ and $R^{13}$ stands for, respectively, an amino, alkyl, alkoxy or hydroxyalkyl radical.

It is further to be understood that a compound wherein $R^2$, $R^3$, $R^{12}$ or $R^{13}$ stands for the hydroxy radical may be obtained by the hydrogenolysis of the corresponding compound wherein $R^2$, $R^3$, $R^{12}$ or $R^{13}$ stands for an α-arylalkoxy radical, for example the benzyloxy radical.

One preferred process for the manufacture of the ethanolamine derivative of the invention comprises the reaction of a compound of the formula:

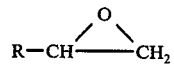

wherein R has the meaning stated above, with an amine of the formula:

$H_2N$—A—NH—X—Y—$R^1$ wherein A, $R^1$, X and Y have the meanings stated above.

A second, and more particularly preferred, process for the manufacture of the ethanolamine derivative of the invention comprises the reaction of a compound of the formula:

R—CHOH.$CH_2NR^8$—A—$NH_2$ wherein R, $R^8$ and A have the meanings stated above, with a compound of the formula:

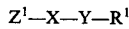

$Z^1$—X—Y—$R^1$ wherein $R^1$, X, Y and $Z^1$ have the meanings stated above. Preferably in this reaction $R^8$ is the hydrogen atom or the benzyl radical, and $Z^1$ is a halogen atom, an alkoxy radical, for example the methoxy or ethoxy radical, or the oxygen atom of an anhydride group.

Optically-active forms of the ethanolamine derivative of the invention may be obtained by the resolution by conventional means of the corresponding racemic ethanolamine derivative of the invention.

The said resolution may be carried out by reacting the racemic ethanolamine derivative with an optically-active acid, followed by fractional crystallisation of the diastereoisomeric mixture of salts thus obtained from a diluent or solvent, for example ethanol, whereafter the optically-active ethanolamine derivative is liberated from the salt by treatment with a base. A suitable optically-active acid is, for example, (+)- or (−)-O,O-di-p-toluoyltartaric acid.

The resolution process may be facilitated by treating the partially resolved ethanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

Alternatively, an optically-active form of an ethanolamine derivative may be obtained by carrying out a process for the manufacture of the ethanolamine derivative using an appropriate optically-active starting material. This procedure is particularly preferred when, apart from the —CHOH— asymmetric centre, there is a further asymmetric centre in the alkylene radical —A— or in the group —Y—$R^1$, and it is a particularly appropriate procedure when used in the series of reactions described under (e) above.

The ethanolamine derivative of the invention in free base form may be converted into an acid-addition salt thereof by reaction with an acid by conventional means.

As stated above, the ethanolamine derivative of the invention or an acid-addition salt thereof possesses $\beta$-adrenergic blocking activity, and in some of the ethanolamine derivatives this activity is cardio-selective. The $\beta$-adrenergic blocking activity may be determined by the reversal of isoprenaline-induced tachycardia in rats or cats, a standard test for the determination of $\beta$-adrenergic blocking activity, and the cardio-selectivity may be determined by the relative freedom from antagonism of isoprenaline-induced vasodilatation in cats or of the relief produced by isoprenaline or histamine-induced bronchospasm in guinea-pigs.

A preferred ethanolamine derivative of the invention is five to 20 times more active as a $\beta$-adrenergic blocking agent then practolol. At doses of an ethanolamine derivative of the invention which produce effective $\beta$-adrenergic blockade in rats or cats, no symptoms of toxicity are apparent.

Some of the ethanolamine derivatives of the invention possess partial $\beta$-adrenoceptor agonist activity as well as the ability to block the action of exogenous and endogenous $\beta$-adrenergic stimulants. This secondary activity is in some cases sufficiently marked for the ethanolamine derivative to be useful for the relief of bronchospasm and for the dilatation of blood vessels with concomitant lowering of blood pressure.

The ethanolamine derivative of the invention may be administered to warm-blooded animals, including man, in the form of a pharmaceutical composition comprising as active ingredient at least one ethanolamine derivative of the invention, or an acid-addition salt thereof, in association with a pharmaceutically-acceptable diluent or carrier therefor.

A suitable composition is, for example a tablet, capsule, aqueous or oily solution or suspension, emulsion, injectable aqueous or oily solution or suspension, dispersible powder, spray or aerosol formulation.

The pharmaceutical composition may contain, in addition to the ethanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis perparations; $\alpha$-adrenergic blocking agents, for example phentolamine and sympathomimetic bronchodilators, for example isoprenaline, orciprenaline, adrenaline and ephedrine.

When used for the treatment of heart diseases, for example angina pectoris and cardiac arrhythmias, or for the treatment of bronchospasm, hypertension or anxiety states in man, it is expected that the ethanolamine derivative would be given to man at a total oral dose of between 20 mg. and 600 mg. daily, at doses spaced at 6–8 hourly intervals, or at an intravenous dose of between 1 mg. and 20 mg. Preferred oral dosage forms are tablets or capsules containing between 10 and 100 mg., and preferably 10 mg. or 40 mg. of active ingredient. Preferred intravenous dosage forms are sterile aqueous solutions of the ethanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of ethyl 2-p-chlorophenylthiazol-4-yl-acetate (2.82 g.) and 2-$\beta$-aminoethylamino-1-phenylethanol (1.8 g.) is heated at 90° C. for 18 hours and then cooled. The residue is crystallised from ethyl acetate and there is thus obtained 2-$\beta$-(2-p-chlorophenylthiazol-4-ylacetamido)ethylamino-1-phenylethanol, m.p. 98°–100° C.

EXAMPLE 2

A mixture of 2-bromoacetylbenzo[b]furan (2.39 g.), N-$\beta$-aminoethylisobutyramide (3.9 g.), methanol (50 ml.) and dimethylformamide (40 ml.) is stirred at 10° C. until a complete solution has been effected. Aqueous 11N-hydrobromic acid (1.88 ml.) is added, and sodium borohydride (0.4 g.) is then added portionwise during 15 minutes. The mixture is stirred at 10° C. for a further 1 hour, acidified with aqueous 11N-hydrochloric acid and then evaporated nearly to dryness under reduced pressure. Water (150 ml.) and ethyl acetate (100 ml.) are added, the mixture is shaken and the aqueous phase is separated, washed three times with ethyl acetate (50 ml. each time) and then basified to pH 12 with aqueous 11N-sodium hydroxide solution. The mixture is extracted three times with ethyl acetate (75 ml. each time) and the combined extracts are dried and evaporated to dryness. The residue is triturated with ether, and the solid product is filtered off and crystallised from ethyl acetate. There is thus obtained 1-(benzo[b]fur-2-yl)-2-($\beta$-isobutyramidoethylamino)ethanol, m.p. 106°–108° C.

EXAMPLE 3

The process described in Example 1 is repeated except that the appropriate 2-$\beta$-aminoethylamino-1-substituted ethanol is used in place of 2-$\beta$-aminoethylamino 1-phenylethanol and the appropriately-substituted ethyl acetate is used in place of ethyl 2-p-chlorophenylthiazol-5-ylacetate. There are thus obtained the compounds described in the following table:

R-CHOH.CH₂NH(CH₂)₂NHCOCH₂R¹

| R | R¹ | m.p. (° C.) | Crystallisation solvent |
|---|---|---|---|
| p-tolyl | 2-methylthiazol-4-yl | 99–100 | ethyl acetate |
| phenyl | 2-thienyl | 97–99 | ethyl acetate |
| phenyl | 5-p-chlorophenylfur-2-yl | 116–117 | ethyl acetate |
| benzodioxol-5-yl | benzimidazol-2-yl | 155–157 | acetonitrile |
| benzodioxol-5-yl | 3-indolyl | 122–124 | acetonitrile |

EXAMPLE 4

The process described in Example 2 is repeated except that the appropriate 2-bromoacetyl intermediate is used in place of 2-bromoacetylbenzo[b]furan and the appropriate N-β-aminoethylamide is used in place of N-β-aminoethylisobutyramide. There are thus obtained the compounds described in the following table:

R-CHOH.CH₂NH(CH₂)₂NHCOR¹

| R | R¹ | m.p.(° C.) | Crystallisation solvent |
|---|---|---|---|
| 2-naphthyl | 2-methylthiazol-4-yl | 101–103 | ethyl acetate |
| benzo[b]thien-3-yl | isopropyl | 124–125 | ethyl acetate |
| benzo[b]furan-2-yl | ethyl | 132–133 | ethyl acetate |

EXAMPLE 5

A mixture of 1-(benzodioxan-2yl)-1,2-epoxyethane (1.8 g.), N-β-aminoethylisobutyramide (1.3 g.) and isopropanol (50 ml.) is heated under reflux for 18 hours and then evaporated to dryness under reduced pressure. The residue is stirred with ether (50 ml.) and the mixture is extracted twice with water (50 ml. each time). The ethereal phase is dried over anhydrous magnesium sulphate and evaporated to dryness under reduced pressure, and the residue is triturated with ether (25 ml.) and the mixture is filtered. The solid residue is crystallised from ethyl acetate and there is thus obtained 1-(benzodioxan-2-yl)-2-(β-isobutyramidoethylamino)ethanol, m.p. 141°–143° C.

EXAMPLE 6

A mixture of N-(2-aminopropyl)phenylacetamide (1.92 g.) 1-(benzofuran-2-yl)-1,2-epoxyethane (1.6 g.) and ethanol (50 ml.) is heated under reflux for 2 hours and then evaporated to dryness under reduced pressure. The residue is chromatographed on a silica gel column (60 cm. × 4.5 cm containing 200 g. of Merck Kieselgel GF 60F254) using a 1:4 v/v mixture of methanol and chloroform as eluant. The eluate containing a substance which has an Rf of 0.3 on similar thin-layer chromatography plates is collected and the solution is evaporated to dryness under reduced pressure. The residue is crystallised from toluene and there is thus obtained 1-(benzofuran-2-yl)-2-(1-methyl-2-phenylacetamidoethyl-)aminoethanol, m.p. 119°–121° C.

What we claim is:

1. An ethanolamine derivative selected from the group consisting of a compound of the formula:

R—CHOH.CH₂NH—A—NH—X—Y—R¹ wherein A is alkylene of from 2 to 12 carbon atoms; wherein X is carbonyl (—CO—) or sulphonyl (—SO₂—); wherein Y is a direct link, or alkylene or alkyleneoxy each of up to 6 carbon atoms, or imino (—NH—), or alkylimino, iminoalkylene, iminoalkyleneoxy or iminoalkylenecarbonyloxy each of up to 6 carbon atoms, or (except when R¹ is hydrogen) is oxygen; and wherein R is benzothienyl, benzodioxanyl, or benzofuryl which is unsubstituted or which contains one or more substituents selected from halogen and alkyl of up to 6 carbon atoms, and R¹ is hydrogen, or alkyl, alkenyl, halogenoalkyl or cycloalkyl each of up to 6 carbon atoms, or benzothienyl, benzodioxanyl, or benzofuryl as defined above for R, or is aryl of the formula:

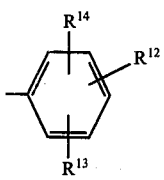

wherein R¹² and R¹³, which may be the same or different, each is hydrogen, halogen, hydroxy, amino, nitro or cyano, or alkyl, hydroxyalkyl, cycloalkyl, alkenyl, alkynyl, alkoxy, alkylthio, cycloalkoxy, alkenyloxy, alkynyloxy or alkanoyl each of up to 6 carbon atoms, or aryl, aryloxy or dialkylamino each of up to 12 carbon atoms; or wherein R¹² and R¹³ together form trimethylene, tetramethylene, 1-oxotetramethylene, propenylene, but-2-enylene or buta-1,3-dienylene such that together with the adjacent benzene ring they form respectively indanyl, 5,6,7,8-tetrahydronaphthyl, 5-oxo-5,6,7,8-tetrahydronaphthyl, indenyl, 5,8-dihydronaphthyl or naphthyl, wherein R¹⁴ is hydrogen or amidic of the formula:

R¹⁵R¹⁶N—CO—Q—

R¹⁵R¹⁶N—CO—NH—Q—

R¹⁵R¹⁶N—CO—Q¹—O— or

R¹⁶—X—NR¹⁵—Q— wherein Q is a direct link or alkylene or alkenylene each of up to 6 carbon atoms; wherein Q¹ is alkylene of up to 6 carbon atoms; wherein R¹⁵ is hydrogen or alkyl of up to 6 carbon atoms; wherein R¹⁶ is hydrogen, alkenyl, cycloalkyl, hydroxyalkyl, or alkoxyalkyl each of up to 6 carbon atoms, or alkyl, aryl, aralkyl or aralkenyl each of up to 10 carbon atoms; and a non-toxic pharmaceutically-acceptable acid-addition salt thereof.

2. An ethanolamine derivative as claimed in claim 1 selected from the group consisting of a compound of the formula given in claim 1 wherein A is ethylene, 1-methyl-ethylene or 1,1-dimethylethylene, wherein R is benzofuryl, benzodioxanyl, or benzothienyl wherein R¹ is unsubstituted phenyl or alkyl of up to 6 carbon atoms, wherein X is carbonyl and wherein Y is a direct link or methylene, and a non-toxic pharmaceutically-acceptable acid-addition salt thereof.

3. An ethanolamine derivative as claimed in claim 2 wherein R is 2-benzo[b]furyl, 3-benzo[b]thienyl or 1,4-benzodioxan-2-yl, and wherein the group —Y—R¹ is ethyl, isopropyl or benzyl, or an acid-addition salt thereof.

4. A compound selected from the group consisting of 1-(benzo[b]fur-2-yl)-2-(β-isobutyramidoethyl)aminoethanol, 1-(benzo[b]fur-2-yl)-2-β-(propionamidoethyl)aminoethanol, 1-(1,4-benzodioxan-2-yl)-2-(β-isobutyramidoethyl)aminoethanol and 1-(benzo[b]fur-2-yl)-2-(1-methyl-2-phenylacetamidoethyl)aminoethanol and a non-toxic pharmaceutically-acceptable acid-addition salt thereof.

5. A compound selected from the group consisting of 1-(benzo[b]fur-2-yl)-2-(β-isobutyramidoethyl)aminoethanol, and a non-toxic pharmaceutically-acceptable acid-addition salt thereof.

6. A compound selected from the group consisting of 1-(benzo[b]fur-2-yl)-2-β-(propionamidoethyl) aminoethanol and a non-toxic pharmaceutically-acceptable acid-addition salt thereof.

7. A compound selected from the group consisting of 1-(benzo[b]fur-2-yl)-2-(1-methyl-2-phenylacetamidoethyl)aminoethanol and a non-toxic pharmaceutically-acceptable acid-addition salt thereof.

8. An acid-addition salt as claimed in claim 1 which is a hydrochloride, hydrobromide, phosphate, sulphate, oxalate, lactate, tartrate, acetate, salicylate, citrate, benzoate, β-naphthoate, adipate or 1,1-methylene-bis-(2-hydroxy-3-naphthoate), or a salt derived from a sulphonated polystyrene resin.

9. A pharmaceutical composition useful for the treatment of prophylaxis of heart diseases and hypertension in a warm blooded animal comprising as active ingredient an effective amount of at least one ethanolamine derivative or an acid-addition salt thereof, claimed in claim 1, in association with a pharmaceutically-acceptable diluent or carrier therefor.

10. A method for the treatment or prophylaxis of heart diseases and hypertension in a warm-blooded animal which comprises administering to said animal an effective amount of at least one compound claimed in claim 1.

11. A method for producing coronary β-adrenergic blockade in a warm-blooded animal in need of such blockade which comprises administering to said animal an effective amount of at least one compound claimed in claim 1.

* * * * *